United States Patent [19]

Torii et al.

[11] Patent Number: 4,622,178

[45] Date of Patent: Nov. 11, 1986

[54] PROCESS FOR PREPARING AZETIDINONE DERIVATIVES

[75] Inventors: Shigeru Torii; Hideo Tanaka; Junzo Nogami, all of Okayama; Michio Sasaoka, Tokushima; Norio Saito, Tokushima; Takashi Shiroi, Tokushima, all of Japan

[73] Assignee: Otsuka Kagaku Kabushiki Kaisha, Osaka, Japan

[21] Appl. No.: 608,695

[22] PCT Filed: Sep. 6, 1983

[86] PCT No.: PCT/JP83/00298

§ 371 Date: May 1, 1984

§ 102(e) Date: May 1, 1984

[87] PCT Pub. No.: WO84/00960

PCT Pub. Date: Mar. 15, 1984

[30] Foreign Application Priority Data

Sep. 6, 1982 [JP] Japan .................. 57-155674

[51] Int. Cl.[4] .................. C07D 205/08; C07D 403/12; C07D 401/12; C07D 401/14
[52] U.S. Cl. .................. 540/358; 546/187; 546/193; 546/194; 546/198; 546/199; 546/209; 546/210; 546/208; 546/256; 546/270; 546/275; 546/276; 546/277; 540/355
[58] Field of Search .................. 260/239 A, 245.4; 546/187, 193, 194, 198, 199, 208, 209, 256, 270, 275, 276, 237, 210

[56] References Cited

FOREIGN PATENT DOCUMENTS 47-9025 5/1972 Japan .
47-9026 5/1972 Japan .
1410371 1/1973 United Kingdom .......... 260/239 A

OTHER PUBLICATIONS

Bennett, "Concise Chemical & Technical Dictionary", 3rd Edition 1974, p. 559.
Micetich et al, Can J. Chem 59, 1020 (1981).

*Primary Examiner*—Mark L. Berch
*Attorney, Agent, or Firm*—Armstrong, Nikaido, Marmelstein & Kubovcik

[57] ABSTRACT

A process for preparing an azetidinone derivative represented by the formula

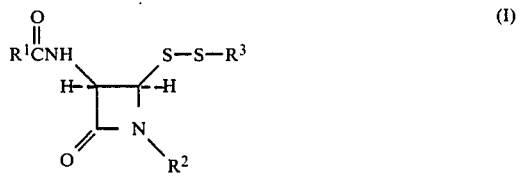

wherein $R^1$ represents a straight-chain or branched-chain lower alkyl group, substituted or unsubstituted aryl group, substituted or unsubstituted phenylmethyl group or substituted or unsubstituted phenyloxymethyl group, $R^2$ represents hydrogen atom, an optionally substituted hydrocarbon residue or protective group for amino group selected from the class consisting of acyl, silyl, sulfonyl and phosphonyl derived from organic or inorganic acid, and $R^3$ represents a substituted or unsubstituted aryl group or the residue of substituted or unsubstituted heterocyclic ring.

9 Claims, No Drawings

PROCESS FOR PREPARING AZETIDINONE DERIVATIVES

TECHNICAL FIELD

This invention relates to a process for preparing azetidinone derivatives and more particularly to a process for preparing azetidinone derivatives represented by the formula

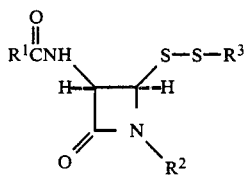
(I)

wherein $R^1$ represents a straight-chain or branched-chain lower alkyl group, substituted or unsubstituted aryl group, substituted or unsubstituted phenylmethyl group or substituted or unsubstituted phenyloxymethyl group, $R^2$ represents hydrogen atom, an optionally substituted hydrocarbon residue or protective group for amino group selected from the class consisting of acyl, silyl, sulfonyl and phosphonyl derived from organic or inorganic acid, and $R^3$ represents a substituted or unsubstituted aryl group or the residue of substituted or unsubstituted heterocyclic ring.

The azetidinone derivatives of the formula (I) are important compounds as intermediates for synthesizing cephalosporin-type antibiotics.

Conventional processes for preparing the azetidinone derivatives of the formula (I) include those which involve the reaction between thiol and sulfenic acid formed by thermal decomposition of penicillin sulfoxide, for example, the reaction of penicillin G-S-oxide with 2-mercaptobenzothiazole [T. Kamizya et al., Tetrahedron Lett., 3001 (1973)]. With this process, however, the amino-protecting group $R^2$ of the compound (I) is restricted by the substituents of the penicillin which is one of the reactants. Processes are known for synthesizing the compounds (I) having various amino-protecting groups $R^2$ for amino which processes comprise reacting a thiazolinoazetidinone derivative having the corresponding amino-protecting groups $R^2$ with a sulphenyl halide in a hydrous organic solvent [S. Torii et al., Tetrahedron Lett., 2495 (1982)]. However, this process involves the preparation of a sulfenyl halide by reacting the corresponding disulfide or thiol with a halogen such as chlorine or bromine and thus entails complicated reaction operation. Further the process requires an excess amount of a sulfenyl halide because of its decomposition in a hydrous solution and involves a cumbersome treatment for separating the decomposed sulfenyl halide. For these reasons, the process poses problems in terms of commercial mass production.

We have conducted extensive research to develop a process using disulfide serving as an agent for converting the starting material to sulfenyl without employing halogen and found that the contemplated compound can be prepared by a simple procedure of reacting a compound having the skeleton of 7-oxo-4-thia-2,6-diazabicyclo[3,2,0]hepto-2-ene with an acid in a hydrous organic solvent in the presence of dibenzothiazolyldisulfide. The invention has been accomplished based on this novel finding.

DISCLOSURE OF THE INVENTION

This invention provides a process for preparing an azetidinone derivative represented by the formula

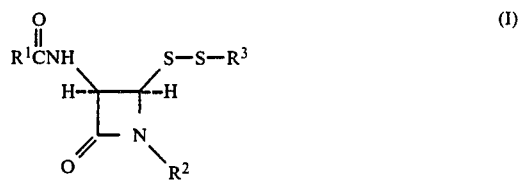
(I)

wherein $R^1$ represents a straight-chain or branched-chain lower alkyl group, substituted or unsubstituted aryl group, substituted or unsubstituted phenylmethyl group or substituted or unsubstituted phenyloxymethyl group, $R^2$ represents hydrogen atom, an optionally substituted hydrocarbon residue or amino-protecting group selected from the class consisting of acyl, silyl, sulfonyl and phosphonyl derived from inorganic or organic acid, and $R^3$ represents a substituted or unsubstituted aryl group or the residue of substituted or unsubstituted heterocyclic ring, the process comprising reacting a thiazolinoazetidinone derivative represented by the formula

(II)

wherein $R^1$ and $R^2$ are as defined above with a sulphur-containing compound represented by the formula

$R^3$—S—Y  (III)

wherein $R^3$ is as defined above and Y represents —$SR^3$ or

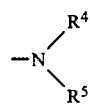

(in which $R^3$ is as defined above and $R^4$ and $R^5$ each represent a cyclic or acyclic amine residue or imido residue) in the presence of an acid in a hydrous organic solvent.

The process of this invention eliminates the need to use a sulfenyl halide which requires special care in handling and gives the contemplated compound in a high yield by carrying out a simple procedure under mild conditions. This process facilitates the separation and purification of the contemplated compound (I) and is significantly advantageous in feasibility of commercial mass production.

The starting compounds of the formula (II) to be used in the reaction of this invention can be any of the compounds having the skeleton of 7-oxo-4-thia-2,6-diazabicyclo[3,2,0]hepto-2-ene and possessing substituents which do not undergo undesired change when reacted under the conditions of this invention. Examples of the groups represented by $R^1$ are methyl, ethyl, isopropyl, butyl, pentyl, hexyl and like straight-chain or branched-chain lower alkyl groups; phenyl, p-nitrophenyl, p-chlorophenyl and like substituted or unsubstituted aryl groups; benzyl, p-nitrophenylmethyl, p-chlorophenylmethyl, p-methoxyphenylmethyl, diphenylmethyl and like substituted or unsubstituted phenylmethyl groups; phenoxymethyl, p-nitrophenoxymethyl, p-chlorophenoxymethyl and like substituted or unsubstituted phenyloxymethyl groups; etc.

The atom represented by $R^2$ is hydrogen and examples of the groups $R^2$ are amino-protecting groups such as acyl, silyl, sulfonyl and phosphonyl derived from inorganic or organic acid and optionally substituted hydrocarbons, etc. Examples of acyl, silyl, sulfonyl, phosphonyl and like amino-protecting groups derived from inorganic or organic acid are acetyl, propionyl, butyryl, trimethylsilyl, dimethylbutylsilyl, methanesulfonyl, ethanesulfonyl, phenylsulfonyl, p-toluenesulfonyl, diphenylphosphonyl, dibenzylphosphonyl, diethylphosphonyl, etc. Exemplary of the substituted hydrocarbons are those of the formulae

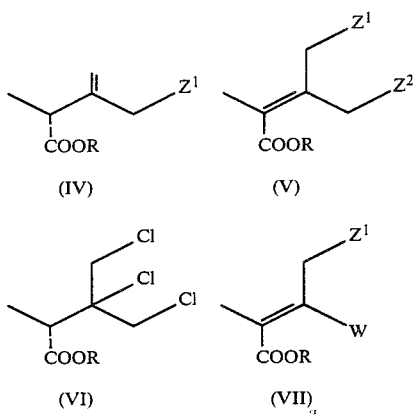

(IV)  (V)  (VI)  (VII)

In the formulae (IV) to (VII), R is hydrogen atom or carboxyl-protecting group, $Z^1$ and $Z^2$ are the same or different and are each hydrogen atom, halogen atom, sulphur group, oxygen group, nitrogen group or the like and W is a protected hydroxyl group. Representative of the carboxyl-protecting groups represented by R are benzyl, p-methoxybenzyl, trimethoxybenzyl, trimethoxydichlorobenzyl, piperonyl, diphenylmethyl, bis(p-methoxyphenyl)methyl, ditolylmethyl, phenyl-p-methoxyphenylmethyl, α-p-methoxyphenylethyl, α-p-methoxyphenyl-β-trichloroethyl, trichloroethyl, florenyl, tert-butyl, trityl, α-diphenylethyl, cumyl, p-nitrobenzyl, o-nitrobenzyl, o,p-dinitrobenzyl, phenacyl, p-bromophenacyl, 1-methoxycarbonyl-2-oxopropyl, methoxyethoxymethyl, methoxymethyl, benzyloxymethyl, isopropoxymethyl, etc. Examples of the substituents represented by $Z^1$ and $Z^2$ are bromine, chlorine, fluorine and like halogen atoms; methylthio, ethylthio, phenylthio, p-nitrophenylthio, pentachlorophenylthio, 2-pyridylthio, 2-benzothiadiazolylthio, 1,3,4-thiadiazole-5-ythio, 2-substituted-1,3,4-thiadiazole-5-ylthio, 1,2,3,4-tetrazole-5-ylthio, 1-substituted-1,2,3,4-tetrazole-5-ylthio, o-ethyldithiocarbonate, N,N-diethyldithiocarbamate, phenylsulfonyl, p-methylphenylsulfonyl and like sulphur groups; hydroxy, methoxy, ethoxy, acetoxy, benzoyloxy, nitrosoxy, nitryloxy, and like oxygen groups, dimethylamino, piperidine-1-yl and like nitrogen groups; etc. Examples of the protected hydroxyl groups represented by W are diphenylphosphonyloxy, methanesulfonate, N-morphonyl, diphenylmethyloxy, etc.

The starting material (II) can be prepared by reacting the corresponding ester of penicillin-1-oxide of the formula (VIII) with more than an equivalent of trimethylphosphorous acid with refluxing in benzene as a solvent, as shown below in a reaction equation or by further treating the reaction product resulting from the foregoing procedure according to a conventional method [S. Torii et al., Tetrahedron Lett., 3198 (1981)].

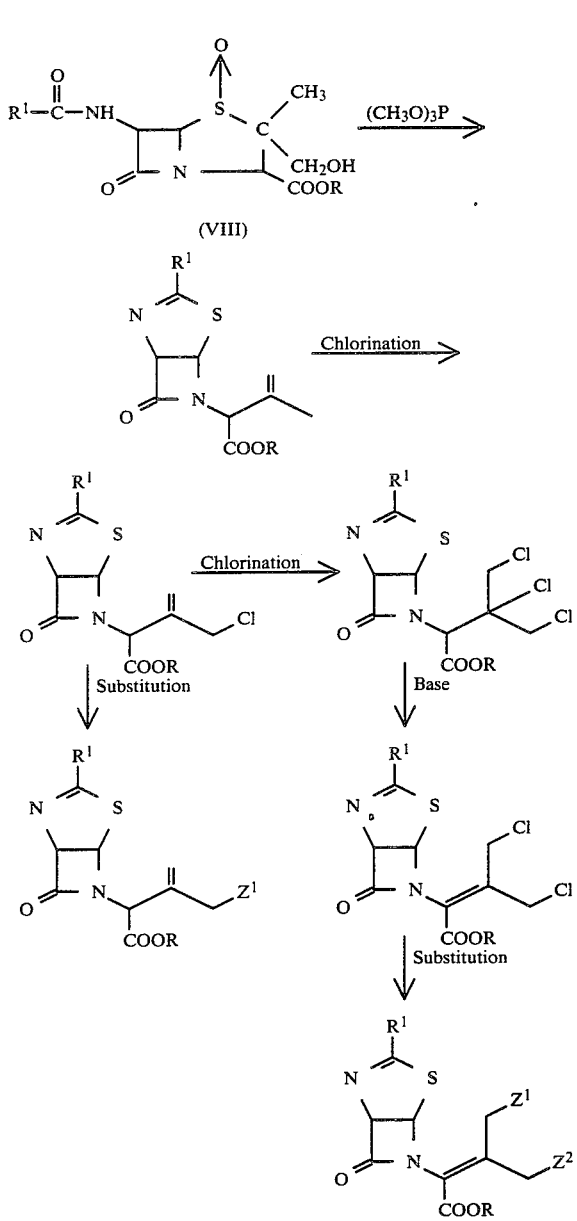

Illustrative of the sulphur-containing compounds of the formula $R^3$—S—Y (wherein $R^3$ and Y are as defined above) which are used in the reaction of the invention are a disulfide wherein Y is —S—$R^3$, sulfenamido wherein Y is

and sulfenimido. Representative of the groups $R^3$ are phenyl, p-nitrophenyl, pentachlorophenyl and like substituted or unsubstituted aryl groups; 2-pyridyl, 2-benzothiazolyl, 1,3,4-thiadiazole-5-yl, 2-methyl-1,3,4-thiadiazole-5-yl, 1,2,3,4-tetrazole-5-yl, 1-methyl-1,2,3,4-tetrazole-5-yl, 1-phenyl-1,2,3,4-tetrazole-5-yl, benzimidazole and like substituted or unsubstituted heterocyclic rings; etc. Examples of the groups

are diethylamine, diisopropylamine and like primary or secondary amine residues; cyclohexylamine, morpholine, piperidine, pyrrolidine, and like cyclic amine residues; phthalimido, succinimido and like imido residues; etc.

The ratio between the compound (II) and the compound (III) is not particularly limited and accordingly can be suitably determined over a wide range. The latter is used in an amount of usually about 1 to about 10 moles, preferably about 1 to 2 moles, per mole of the former.

The reaction of this invention is conducted in a hydrous organic solvent in the presence of an acid. The water content in the hydrous organic solvent is not particularly restricted but is usually 1 to 1000 equivalents, preferably about 10 to about 500 equivalents, relative to the compound (II). Suitable organic solvents include, for example, pentane, hexane, benzene, toluene and like hydrocarbons; methylene chloride, chloroform, carbon tetrachloride, dichlorobenzene and like halogenated hydrocarbons; methyl formate, methyl acetate, ethyl acetate, butyl acetate and like esters; diethyl ether, dimethyl ether, tetrahydrofuran, dioxane and like ethers; methanol, ethanol, butanol, ethylene glycol and like alcohols; formic acid, acetic acid, propionic acid and like carboxylic acids; acetonitrile, benzonitrile and like nitriles; dimethylformamide, dimethylacetamide and like amides; dimethylsulfoxide and like sulfoxides; nitromethane, nitroethane and like nitrohydrocarbons; acetone, cyclohexane and like ketones; etc. These solvents are used singly or in mixture. Preferred examples of useful organic solvents are ethers, ketones, alcohols, amides, sulfoxides and like hydrophilic polar solvents or a mixture of other class of solvent and such hydrophilic solvent. The amount of the solvent, although variable with the selection of the compounds (II) and (III), is usually 1 to 1000 parts, preferably 2 to 500 parts, per part of the compound (II).

Examples of useful acids are hydrogen halogenide, sulphuric acid, nitric acid, phosphoric acid, perchloric acid, chloric acid and like mineral acids; alkanesulfonic acid, arylsulfonic acid, aralkylsulfonic acid, α-haloalkanesulfonic acid and like sulfonic acids; α-halocarboxylic acid, polycarboxylic acid and like carboxylic acids; etc. among which those having a dissociation constant of about over 0.01 are preferred. Representative of such preferred acids are perchloric acid, trifluoroacetic acid, trichloroacetic acid, dichloroacetic acid, trifluoromethanesulfonic acid, trichloromethanesulfonic acid, hydrochloric acid, hydrobromic acid, sulphuric acid, hydrofluoric acid, nitric acid, phosphoric acid, benzenesulfonic acid, toluenesulfonic acid, etc. The amount of the acid, although variable with the selection of the compounds (II) and (III) and the solvent, reaction temperature and other conditions, is usually about 0.01 to about 50 moles, preferably about 0.1 to about 10 moles, per mole of the substrate.

When a side reaction is caused by the decomposition of an azetidinone ring and an amino-protecting group $R^2$ and the like, the contemplated compound can be produced in high yields by appropriately determining the class and concentration of the acid, reaction temperature, reaction time and like conditions. The reaction of this invention rapidly proceeds at a temperature usually about 0° to about 50° C., preferably about 15° to about 35° C., and is completed usually in about 5 minutes to 1 hour, whereby the contemplated compound can be produced in high yields.

The contemplated compound thus obtained is extracted and isolated in the usual manner after completion of the reaction, and can be easily purified by conventional methods such as precipitation, filteration, recrystallization, chromatography or the like.

Of the present compounds of the formula (I), those wherein $R^1$ is a straight-chain or branched-chain lower alkyl, substituted or unsubstituted aryl, substituted or unsubstituted phenylmethyl, or substituted or unsubstituted phenyloxymethyl, $R^2$ is

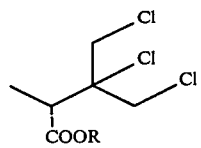

(in which R is hydrogen or carbonyl-protecting group) and $R^3$ is substituted or unsubstituted aryl or the residue of substituted or unsubstituted heterocyclic ring are novel compounds undisclosed in literature.

The azetidinone derivatives prepared by the process of this invention can be each made into a cephalosporin-type antibiotic of the formula (IX) or (X), as indicated below in Reaction Equation-1 and Reaction Equation-2 (cf. Reference Example to be described later).

Reaction Equation - 1

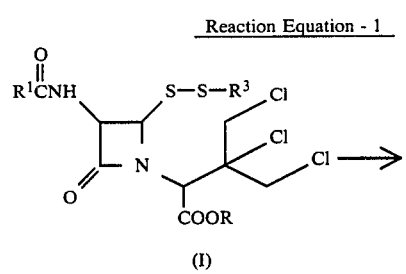

(I)

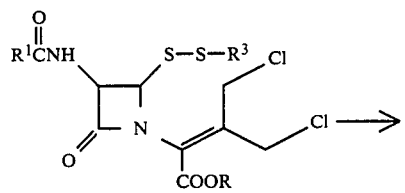

Reaction Equation - 1

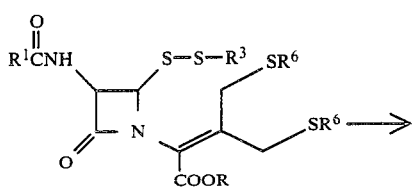

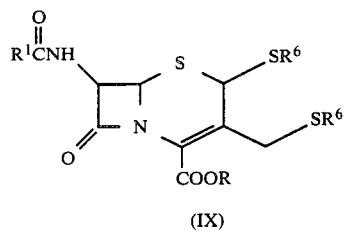

In Reaction Equation-1, $R^1$ $R^3$ and R are as defined above and $R^6$ is a substituted or unsubstituted aryl, the residue of substituted or unsubstituted aromatic heterocyclic ring residue, thiocarboxylic acid residue, thiocarbonic acid residue or thioamido residue.

Reaction Equation - 2

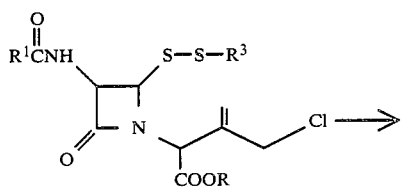

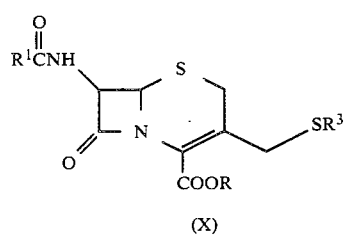

In Reaction Equation-2, $R^1$, R and $R^3$ are as defined above.

Given below are Examples and Reference Example for clarification of the invention.

EXAMPLE 1

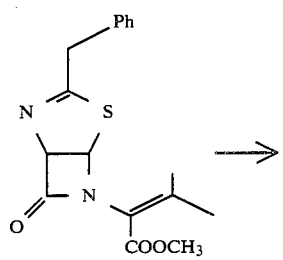

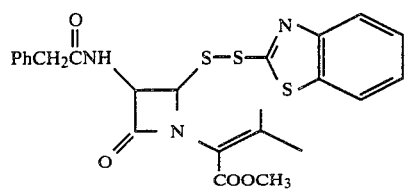

Dispersed in 3 ml of tetrahydrofuran were 54.7 mg of methyl 2-(3-benzyl-7-oxo-4-thia-2,6-diazabicyclo[3,2,0-]hepto-2-ene-6-yl)-3-methyl-2-butenate and 72.0 mg of dibenzothiazolyldisulfide. To the dispersion was added 0.75 ml of a 5% aqueous solution of hydrochloric acid and the mixture was stirred at room temperature for 40 minutes. A 10 ml quantity of ethyl acetate was added to the reaction mixture and the insolubles were removed by a glass filter. The filtrate was washed with water and dried over anhydrous sodium sulfate. The solvent was distilled off to give 133.3 mg of the residue, which was separated and purified by silica gel column chromatography, affording 84.8 mg of methyl 2-(4-(2-benzothiazolyl)dithio-3-phenylacetamide-2-oxoazetidine-1-yl)-3-methyl-2-butenate as white powder in about 100% yield.

IR (CHCl$_3$): 3400, 1770, 1720, 1672 cm$^{-1}$.

NMR (CDCl$_3$): δ(ppm) 2.07 (s, 3H), 2.12 (s, 3H), 3.57 (s, 3H), 3.66 (s, 2H), 5.04 (dd, 1H, 5 Hz, 8 Hz), 5.38 (d, 1H, 5 Hz), 6.66 (d, 1H, 8 Hz), 7.28 (s, 5H), 7.20–7.90 (m, 4H).

EXAMPLES 2 to 24

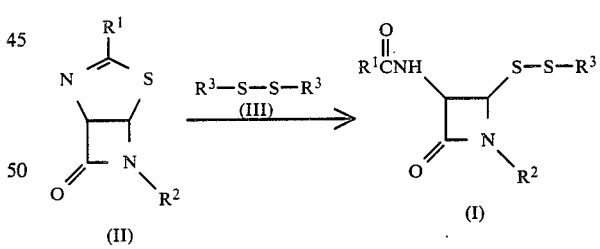

Thiazolinoazetidinone (II) and disulfide (III) were dispersed in tetrahydrofuran and an acid was added to the dispersion. The mixture was stirred at room temperature for a predetermined period of time. The reaction was conducted under the same conditions as Example 1 except those as shown in Table 1 below, followed by the same post-treatment, whereby the contemplated azetidinone derivative (I) was produced.

Table 1 below shows the reaction conditions and yields and Table 2 below indicates IR and $^1$HNMR data.

TABLE 1

| Example | Compound (II) R$^1$ | Compound (II) R$^2$ | Compound (III) R$^3$ | (III/II)* | Acid | Reaction time (min.) | (I) Yield (%) |
|---|---|---|---|---|---|---|---|
| 2 | PhCH$_2$ | =C(CH$_3$)–CH(CO$_2$CH$_2$Ph)– | Br | (1.24) | 5% HCl | 40 | 85 |
| 3 | PhCH$_2$ | =C(CH$_3$)–CH(CO$_2$CH$_2$Ph)– | BT | (1.10) | 10% HClO$_4$ | 40 | 90 |
| 4 | PhCH$_2$ | =C(CH$_3$)–CH(CO$_2$CH$_2$Ph)– | BT | (1.26) | 1N H$_2$SO$_4$ | 40 | 65 |
| 5 | PhCH$_2$ | =C(CH$_3$)–CH(CO$_2$CH$_2$Ph)– | 2-Py | (1.45) | 5% HCl | 40 | 75 |
| 6 | PhCH$_2$ | =C(CH$_3$)–C(CH$_3$)(CO$_2$CH$_3$)– | 2-Py | (1.26) | 5% HCl | 40 | 85 |
| 7 | PhCH$_2$ | =C(CH$_3$)–C(CH$_3$)(CO$_2$CH$_3$)– | C$_5$Cl$_5$ | (1.20) | 5% HCl | 40 | 65 |
| 8 | PhCH$_2$ | =C(CH$_3$)–C(CH$_3$)(CO$_2$CH$_3$)– | BI | (1.37) | 5% HCl | 40 | 55 |
| 9 | PhCH$_2$ | =C(CH$_3$)–C(CH$_3$)(CO$_2$CH$_3$)– | BT | (1.36) | 27% p-TsOH | 40 | 98 |
| 10 | PhCH$_2$ | =C(CH$_3$)–C(CH$_3$)(CO$_2$CH$_3$)– | BT | (1.08) | 13% TFA | 40 | 60 |
| 11 | PhOCH$_2$ | =C(CH$_2$Cl)–CH(CO$_2$CH$_2$Ph)– | BT | (1.40) | 5% HCl | 40 | 81 |
| 12 | PhCH$_2$ | =C(CH$_2$Cl)–CH(CO$_2$CH$_2$Ph)– | BT | (1.40) | 5% HCl | 35 | 99 |
| 13 | PhCH$_2$ | =C(CH$_2$Cl)–CH(CO$_2$CH$_2$Ph)– | CH$_3$-thiadiazolyl (N=N, S) | (1.32) | 5% HCl | 35 | 99 |
| 14 | PhCH$_2$ | =C(CH$_2$OCOCH$_3$)–CH(CO$_2$CH$_2$Ph)– | BT (1.06) | 5% HCl | 20 | 85 | |
| 15 | PhCH$_2$ | =C(CH$_2$SCSOEt)–CH(CO$_2$CH$_2$Ph)– | BT | (1.30) | 5% HCl | 40 | 90 |

TABLE 1-continued

| Example | Compound (II) R¹ | Compound (II) R² | Compound (III) R³ | (III/II)* | Acid | Reaction time (min.) | (I) Yield (%) |
|---|---|---|---|---|---|---|---|
| 16 | PhCH₂ | CH₂—C(=CH₂)—CH(CH₃)—CO₂CH₂Ph with SCN(Me)₂ (C=S) group | BT | (1.30) | 5% HCl | 40 | 93 |
| 17 | PhCH₂ | CH(CH₃)(CO₂CH₂Ph)—CH₂—C(=CH₂)—S—C(=N-N=C(CH₃))—S (thiadiazole) | BT | (1.30) | 5% HCl | 40 | 92 |
| 18 | PhCH₂ | CH(CH₃)(CO₂CH₂Ph)—CH₂—C(=CH₂)—S-tetrazolyl(N-Ph) | BT | (1.30) | 5% HCl | 40 | 89 |
| 19 | PhCH₂ | CH(CH₃)(CO₂CH₂Ph)—CH₂—C(=CH₂)—S-tetrazolyl(N-CH₃) | BT | (1.30) | 5% HCl | 40 | 88 |
| 20 | PhCH₂ | C(=C(CH₂Cl)(Cl))—CO₂CH₂Ph | BT | (1.32) | 5% HCl | 40 | 75 |
| 21 | PhCH₂ | CH(CH₃)—C(CH₂Cl)(Cl)(Cl)—CO₂CH₂Ph | BT | (1.50) | 5% HCl | 40 | 80 |
| 22 | PhCH₂ | CH(CH₃)—C(=CH₂)—COOH | BT | (1.10) | 5% HCl | 40 | 100 |
| 23 | PhCH₂ | H | BT | (1.06) | 5% HCl | 36 | 90 |
| 24 | PhCH₂ | CH(CH₃)(COOCH₂Ph)—C(=CH₂)—OH | BT | (1.06) | 5% HCl | 40 | 85 |

Note:

Ph stands for phenyl group; BT, benzothiazol-2-yl; 2-Py, pyridin-2-yl; C₆Cl₅, pentachlorophenyl;

BI, benzimidazol-2-yl; PNP, NO₂—C₆H₄—, p-nitrophenyl; p-TsOH, p-toluenesulfonic acid;

TFA, trifluoroacetic acid; Et, ethyl.
*The mole of the compound (III) based on the mole of the compound (II) (mole/mole).

TABLE 2

| Compound (I) R¹ | Compound (I) R² | Compound (I) R³ | |
|---|---|---|---|
| PhCH₂ | CH(CH₃)(CO₂CH₂Ph)—C(=CH₂)— | benzothiazol-2-yl | IR (CHCl₃) 3395, 1775, 1740, 1680 cm⁻¹<br>NMR (CDCl₃, δ) 1.90 (s, 3H), 3.65 (s, 2H), 4.95 (s, 1H), 5.01 (s, 1H), 5.15(bs, 3H), 5.32 (dd, 1H), 4.5Hz, 8Hz), 5.53 (d, 1H, 4.5Hz), 6.46 (d, 1H, 8Hz), 7.28 (s, 5H), 7.30 (s, 5H), 7.20-8.00 (m, 4H) |

TABLE 2-continued

| R¹ | R² | R³ | |
|---|---|---|---|
| PhCH₂ | (=CH-CH₃ branch on CH with CO₂CH₂Ph) | 2-pyridyl | IR (CHCl₃) 3400, 1770, 1735, 1670 cm⁻¹<br>NMR (CDCl₃, δ) 1.88 (s, 3H), 3.63 (s, 2H),<br>4.87 (s, 1H), 4.99 (s, 1H), 5.12 (bs, 2H),<br>5.10–5.30 (m, 1H), 5.32 (s, 1H),<br>5.54 (d, 1H, 5Hz), 7.00–7.70 (m, 13H),<br>8.35 (m, 2H) |
| PhCH₂ | =C(CH₃)₂ with CO₂CH₃ | 2-pyridyl | IR (CHCl₃) 3390, 1770, 1720, 1678 cm⁻¹<br>NMR (CDCl₃, δ) 1.98 (s, 3H), 2.15 (s, 3H),<br>3.58 (s, 3H), 3.65 (s, 2H),<br>5.22 (dd, 1H, 5Hz, 8Hz), 5.43 (d, 1H, 5Hz),<br>6.92 (d, 1H, 8Hz), 7.00–7.80 (m, 7H),<br>8.30–8.50 (m, 2H) |
| PhCH₂ | =C(CH₃)₂ with CO₂CH₃ | tetrachlorophenyl | IR (CHCl₃) 3400, 1770, 1727, 1680 cm⁻¹<br>NMR (CDCl₃, δ) 1.95 (s, 3H), 2.06 (s, 3H),<br>3.59 (s, 2H), 3.70 (s, 3H),<br>5.02 (dd, 1H, 5Hz, 8Hz), 5.53 (d, 1H, 5Hz),<br>6.38 (d, 1H, 8Hz), 7.26 (s, 5H) |
| PhCH₂ | =C(CH₃)₂ with CO₂CH₃ | benzimidazol-2-yl | IR (CHCl₃) 3380, 3280, 1770, 1720, 1670 cm⁻¹<br>NMR (CDCl₃, δ) 1.97 (s, 3H), 2.20 (s, 3H),<br>3.58 (s, 3H), 3.72 (s, 2H),<br>4.76 (dd, 1H, 5Hz, 8Hz), 4.96 (d, 1H, 5Hz),<br>6.75 (d, 1H, 8Hz), 7.00–7.50 (m, 10H) |
| PhOCH₂ | =C(CH₂Cl) with CO₂CH₂Ph | benzothiazol-2-yl | IR (neat) 3320, 1775, 1735, 1675 cm⁻¹<br>NMR (CDCl₃, δ) 4.30 (s, 2H), 4.56 (s, 2H),<br>5.21 (s, 2H), 5.20–5.70 (m, 5H),<br>6.70–8.00 (m, 15H) |
| PhCH₂ | =CH-CH₂Cl with CO₂CH₂Ph | CH₃-C(=N-N=)S-C (thiadiazole) | IR (neat) 3280, 1775, 1740, 1665 cm⁻¹<br>NMR (CDCl₃, δ) 2.62 (s, 3H), 3.60 (s, 2H),<br>4.21 (s, 2H), 5.16 (s, 2H), 5.05–5.40 (m, 3H),<br>5.46 (s, 1H), 5.55 (d, 1H, 4.5Hz),<br>7.05 (d, 1H, 8Hz), 7.25 (s, 5H), 7.30 (s, 5H) |
| PhCH₂ | =CH-CH₂Cl with CO₂CH₂Ph | benzothiazol-2-yl | IR (neat) 3280, 1775, 1740, 1665 cm⁻¹<br>NMR (CDCl₃, δ) 3.66 (s, 2H),<br>4.15 and 4.89 (ABq, 2H, 11Hz), 5.14 (s, 2H),<br>5.00–5.40 (m, 3H), 5.50 (s, 1H),<br>5.55 (d, 1H, 4Hz), 6.92 (d, 1H, 8Hz),<br>7.10–7.60 (m, 12H), 7.60–8.00 (m, 2H) |
| PhCH₂ | =CH-CH₂-OC(=O)CH₃ with CO₂CH₂Ph | benzothiazol-2-yl | IR (neat) 3280, 1780, 1745, 1670, 1235 cm⁻¹<br>NMR (CDCl₃, δ) 2.00 (s, 3H), 3.64 (s, 2H),<br>4.70 (s, 2H), 5.11 (bs, 3H),<br>5.18 (dd, 1H, 5Hz, 8Hz), 5.25 (s, 1H),<br>5.46 (s, 1H), 5.48 (d, 1H, 5Hz),<br>6.63 (d, 1H, 8Hz), 7.10–7.60 (m, 12H),<br>7.60–8.00 (m, 2H) |
| PhCH₂ | =CH-CH₂-SC(=S)OEt with CO₂CH₂Ph | benzothiazol-2-yl | IR (neat) 3280, 1780, 1740, 1670 cm⁻¹<br>NMR (CDCl₃, δ) 1.33 (t, 3H, 7Hz), 3.64 (s, 2H),<br>4.01 (s, 2H), 4.56 (q, 2H, 7Hz), 5.12 (s, 2H),<br>5.17 (s, 2H), 5.28 (dd, 1H, 4.5Hz, 8Hz),<br>5.46 (s, 1H), 5.50 (d, 1H, 4.5Hz),<br>6.76 (d, 1H, 8Hz), 7.10–7.60 (m, 12H),<br>7.60–8.00 (m, 2H) |
| PhCH₂ | =CH-CH₂-SC(=S)N(Me)₂ with CO₂CH₂Ph | benzothiazol-2-yl | IR (neat) 3300, 1780, 1745, 1670 cm⁻¹<br>NMR (CDCl₃, δ) 3.31 (bs, 3H), 3.39 (bs, 3H),<br>3.65 (s, 2H), 4.20 and 4.55 (ABq, 2H, 15Hz),<br>5.13 (s, 3H), 5.25 (s, 1H),<br>5.29 (dd, 1H, 4.5Hz, 8Hz), 5.50 (s, 1H),<br>5.52 (d, 1H, 4.5Hz), 6.76 (d, 1H, 8Hz),<br>7.20–7.60 (m, 12H), 7.60–8.00 (m, 2H) |
| PhCH₂ | =CH-CH₂-S-C(=N-N=)-CH₃ (thiadiazole) with CO₂CH₂Ph | benzothiazol-2-yl | IR (neat) 3270, 1780, 1740, 1670 cm⁻¹<br>NMR (CDCl₃, δ) 2.63 (s, 3H), 3.70 (s, 2H),<br>4.19 and 4.26 (ABq, 2H, 15Hz), 5.14 (s, 2H),<br>5.19 (s, 1H), 5.30–5.70 (m, 4H),<br>7.10–7.50 (m, 13H), 7.60–8.00 (m, 2H) |

TABLE 2-continued

| | Compound (I) | | |
|---|---|---|---|
| R¹ | R² | R³ | |
| PhCH₂ | [structure: CH(CH₃)-C(=CH-CH₂-S-tetrazole-N-Ph)-CO₂CH₂Ph] | [benzothiazole] | IR (neat) 3280, 1780, 1740, 1670 cm⁻¹<br>NMR (CDCl₃, δ) 3.68 (s, 2H), 4.30 (s, 2H),<br>5.07 (s, 2H), 5.17 (s, 1H),<br>5.26 (dd, 1H, 4.5Hz, 8Hz), 5.31 (s, 1H),<br>5.55 (d, 1H, 4.5Hz), 5.59 (s, 1H),<br>6.83 (d, 1H, 8Hz), 7.10–7.60 (m, 17H),<br>7.60–8.00 (m, 2H) |
| PhCH₂ | [structure: CH(CH₃)-C(=CH-CH₂-S-tetrazole-N-CH₃)-CO₂CH₂Ph] | [benzothiazole] | IR (neat) 3280, 1780, 1740, 1670 cm⁻¹<br>NMR (CDCl₃, δ) 3.69 (s, 2H), 3.74 (s, 3H),<br>4.19 (bs, 2H), 5.10 (bs, 3H),<br>5.23 (dd, 1H, 4.5Hz, 8Hz), 5.36 (s, 1H),<br>5.48 (s, 1H), 5.57 (d, 1H, 4.5Hz),<br>6.79 (d, 1H, 8Hz), 7.10–7.60 (m, 12H),<br>7.60–8.00 (m, 2H) |
| PhCH₂ | [structure with CH₂Cl groups, CO₂CH₂Ph] | [benzothiazole] | IR (CHCl₃) 3390, 1785, 1720, 1670 cm⁻¹<br>NMR (CDCl₃, δ) 3.68 (s, 2H), 4.68 (bs, 2H),<br>4.73 (bs, 2H), 4.84 (dd, 1H, 5Hz, 7Hz),<br>4.92 and 5.10 (ABq, 2H, 11Hz), 5.44 (d, 1H, 5Hz),<br>6.53 (d, 1H, 7Hz), 7.17 (s, 5H), 7.30 (s, 5H),<br>7.10–7.90 (m, 4H) |
| PhCH₂ | [structure with three Cl substituents, CO₂CH₂Ph] | [benzothiazole] | IR (CHCl₃) 3395, 1783, 1742, 1672 cm⁻¹<br>NMR (CDCl₃, δ) 3.68 (s, 2H),<br>4.18 and 4.34 (ABq, 2H, 13Hz), 4.25 (bs, 2H),<br>4.99 (dd, 1H, 5Hz, 7.5Hz), 5.17 (s, 2H),<br>5.31 (s, 1H), 5.62 (d, 1H, 5Hz),<br>6.28 (d, 1H, 7.5Hz), 7.24 (bs, 5H),<br>7.30 (s, 5H), 7.20–8.00 (m, 4H) |
| PhCH₂ | [structure: CH(CH₃)-C(=CH₂)-COOH] | [benzothiazole] | IR (CHCl₃) 3390, 3280, 1770, 1732, 1675 cm⁻¹<br>NMR (CD₃COCD₃, δ) 1.98 (s, 3H), 3.71 (s, 2H),<br>4.93 (s, 1H), 5.18 (bs, 2H),<br>5.32 (dd, 1H, 5Hz, 8Hz), 5.58 (d, 1H, 5Hz),<br>7.30 (s, 5H), 7.10–7.55 (m, 4H),<br>7.70–8.00 (m, 2H) |
| PhCH₂ | H | [benzothiazole] | IR (nujol) 3280, 1790, 1670 cm⁻¹<br>NMR (CD₃SOCD₃, δ) 3.58 (bs, 2H),<br>5.20–5.30 (m, 2H), 7.23 (s, 5H),<br>7.00–7.60 (m, 2H), 7.60–8.00 (m, 2H),<br>9.10 (m, 2H) |
| PhCH₂ | [structure: CH(CH₃)-C(=CH-CH₂-OH)-COOCH₂Ph] | [benzothiazole] | IR (neat) 3280, 1770, 1735, 1665 cm⁻¹<br>NMR (CDCl₃, δ) 2.70 (bs, 1H), 3.60 (s, 2H),<br>4.26 (s, 2H), 5.10 (s, 2H), 5.05–5.40 (m, 3H),<br>5.49 (d, 1H, 4Hz), 6.84 (d, 1H, 8Hz),<br>7.10–7.60 (m, 12H), 7.60–7.95 (m, 2H) |

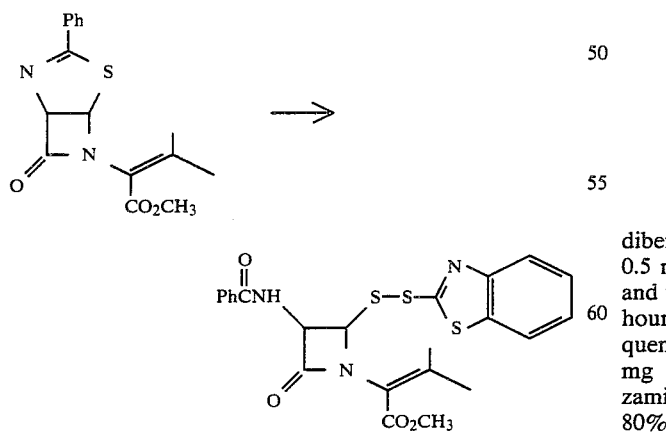

Dispersed in 2 ml of tetrahydrofuran were 42.2 mg of methyl 2-(3-phenyl-7-oxo-4-thia-2,6-diazabicyclo[3,2,0-]hepto-2-ene-6-yl)-3-methyl-2-butenate and 50.2 mg of dibenzothiazolyldisulfide. To the dispersion was added 0.5 ml of a 5% aqueous solution of hydrochloric acid and the mixture was stirred at room temperature for 40 hours. After completion of the reaction, the same subsequent procedure as in Example 1 followed, giving 53.7 mg of methyl 2-(4-(2-benzothiazolyl)dithio-3-benzamido-2-oxo-azetidine-1-yl)-3-methyl-2-butenate in 80% yield.

IR (CHCl₃): 3410, 1772, 1722, 1664 cm⁻¹.

NMR (CDCl₃): δ(ppm) 2.18 (bs, 6H), 3.64 (s, 3H), 5.40 (dd, 1H, 5 Hz, 7 Hz), 5.66 (d, 1H, 5 Hz), 7.15–8.00 (m, 10H).

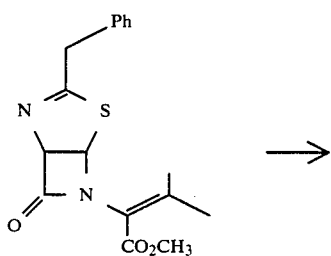

→

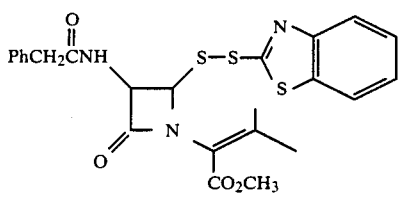

Dispersed in 2 ml of methanol were 41.2 mg of methyl 2-(3-benzyl-7-oxo-4-thia-2,6-diazabicyclo[3,2,0-]hepto-2-ene-6-yl)-3-methyl-2-butenate and 46.5 mg of dibenzothiazolyldisulfide. A 0.5 ml quantity of a 5% aqueous solution of hydrochloric acid was added to the dispersion and the mixture was stirred at room temperature for 40 minutes. The same subsequent procedure as in Example 1 was conducted to provide 49.1 mg of methyl 2-(4-(2-benzothiazolyl)dithio-3-phenylacetamide-2-oxo-azetidine-1-yl)-3-methyl-2-butenate in 75% yield. The product thus obtained was found identical in IR and ¹HNMR data with those of the compound produced in Example 1.

EXAMPLES 27 TO 30

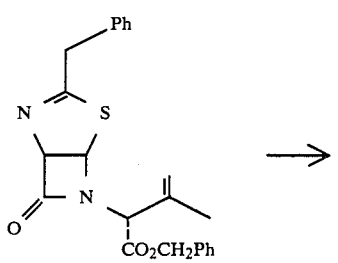

→

-continued

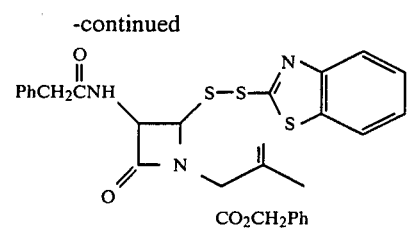

Reaction was conducted between methyl 2-(3-benzyl-7-oxo-4-thia-2,6-diazabicyclo[3,2,0]hepto-2-ene-6-yl)-3-methyl-3-butenate and dibenzothiazolyldisulfide in solvents with the results as shown in Table 3 below. The reaction conditions other than those indicated in Table 3 were the same as Example 1. The compound (I) obtained was found identical in IR and ¹HNMR data with the compound produced in Example 2.

TABLE 3

| Ex. | Compound (II) mg | Compound (III) R³=BT mg | Solvent | ml | 5% HCl | ml | Time (min) | (I) Yield (%) |
|---|---|---|---|---|---|---|---|---|
| 27 | 50.3 | 52.4 | DMF | (3) | 5% HCl | (0.8) | 5 | 55 |
| 28 | 40.7 | 49.9 | MeCN | (2) | 5% HCl | (0.5) | 55 | 63 |
| 29 | 40.5 | 46.9 | MeOH | (2) | 5% HCl | (0.5) | 40 | 58 |
| 30 | 41.1 | 48.1 | CH₃COCH₃ CH₂Cl₂ | (3) (1) | 10% HClO₄ | (0.5) | 40 | 94 |

Note:

BT represents 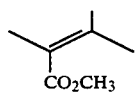 and

DMF stands for demethylformamide; MeCN, acetonitrile; and MeOH, methanol.

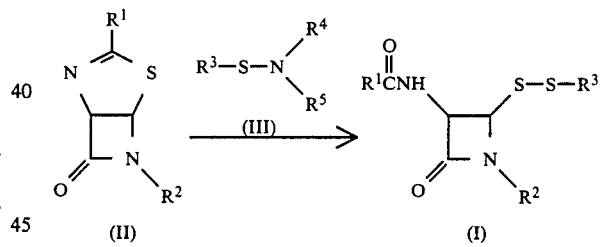

Dissolved in 2 ml of tetrahydrofuran were 41.1 mg of the compound (II) wherein R¹ is CH₂Ph and R² is

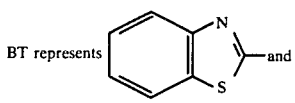

and 30.7 mg of the compound (III) wherein R³ is

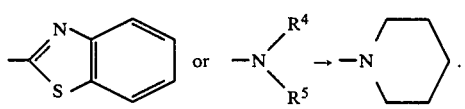

To the solution was added 0.5 ml of a 5% aqueous solution of hydrochloric acid and the mixture was stirred at room temperature for 40 minutes. The reaction mixture was diluted with ethyl acetate. The dilute was washed with a saturated aqueous solution of sodium chloride and dried over anhydrous sodium sulfate.

The solvent was distilled off. The resulting residue was separated and purified by silica gel column chromatography, giving 46.4 mg of a compound (I) wherein R¹ is CH₂PH, R² is

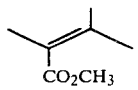

and R³ is

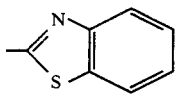

in 72% yield. The compound (I) thus obtained was found identical in IR and ¹HNMR data with the standard compound (I).

EXAMPLES 32 AND 33

Compounds (I) was prepared from compounds (II) and (III) by following the same procedure as Example 30. Table 4 below shows the results. The compounds (I) thus obtained were identical in IR and ¹HNMR data with the standard compound (I).

TABLE 4

| Ex. | Compound (II) R¹ | R² | R³—S—N(R⁴)(R⁵) | Reaction time (Min.) | (I) (%) |
|---|---|---|---|---|---|
| 32 | PhCH₂ | =C(CH₃)–CH(CO₂CH₂Ph)– | BTS—N(morpholine) | 30 | 64 |
| 33 | PhCH₂ | =CH–CH(CO₂CH₂Ph)–CH₂Cl | BTS—N(morpholine) | 30 | 51 |

EXAMPLES 34 TO 57

The procedure of Example 1 was repeated, producing the compounds (I) as shown below in Table 5 which also indicates IR and ¹HNMR data of the compounds (I) thus obtained.

TABLE 5

Compound (I): R¹CONH-[β-lactam]-S-S-R³, N-R²

| Ex. | R¹ | R² | R³ | IR and ¹HNMR Data |
|---|---|---|---|---|
| 34 | PhCH₂ | C(=C(CH₃)(CO₂CH₃))(CH₂Cl)(CH₂SO₂Ph) | benzothiazolyl | IR (CDCl₃) 3390, 1783, 1723, 1670 cm⁻¹ NMR (400MHz, CDCl₃, δ) 3.38 (s, 3H), 3.75 (ABq, 2H, 16.4Hz), 4.24 and 4.84 (ABq, 2H, 12.6Hz), 4.45 and 5.10 (ABq, 2H, 14.0Hz), 4.95 (dd, 1H, 5.3Hz, 7.5Hz), 5.48 (d, 1H, 5.3Hz), 6.36 (d, 1H, 7.5Hz), 7.30 (s, 5H), 7.30–7.95 (m, 5H) |
| 35 | PhCH₂ | C(=C(CH₃)(CO₂Me))(CH₂SO₂Ph)(CH₂SO₂Ph) | benzothiazolyl | IR (CHCl₃) 3390, 1780, 1723, 1672 cm⁻¹ NMR (CDCl₃, δ) 3.39 (s, 3H), 3.68 (bs, 2H), 4.09 and 4.89 (ABq, 2H, 15Hz), 4.88 and 5.36 (ABq, 2H, 14Hz), 4.99 (dd, 1H, 5Hz, 8Hz), 5.46 (d, 1H, 5Hz), 6.77 (d, 1H, 8Hz), 7.10–8.10 (m, 19H) |
| 36 | PhCH₂ | C(=C(CH₃)(CO₂Me))(CH₂SCSOEt)(CH₂SCSOEt) | benzothiazolyl | IR (CHCl₃) 3400, 1780, 1724, 1675 cm⁻¹ NMR (CDCl₃, δ) 1.40 (t, 6H, 7Hz), 3.56 (s, 3H), 3.74 (bs, 2H), 4.34 and 4.54 (ABq, 2H, 13Hz), 4.50 (bs, 2H), 4.67 (q, 4H, 7Hz), 5.13 (dd, 1H, 5Hz, 8Hz), 5.59 (d, 1H, 5Hz), 6.59 (d, 1H, 8Hz), 7.37 (s, 5H), 7.20–8.00 (m, 4H) |
| 37 | PhCH₂ | C(=C(CH₃)(CO₂CH₃))(CH₂SBT)(CH₂SBT) | benzothiazolyl | IR (CHCl₃) 3390, 1778, 1720, 1672 cm⁻¹ NMR (CDCl₃, δ) 3.59 (s, 3H), 3.68 (s, 2H), 4.70 and 4.91 (ABq, 2H, 13Hz), 4.83 (bs, 2H), 5.17 (dd, 1H, 5Hz, 8Hz), 5.63 (d, 1H, 5Hz), 6.75 (d, 1H, 8Hz), 7.10–8.00 (m, 17H) |

TABLE 5-continued $$\text{R}^1\text{CONH}-\overset{\displaystyle S-S-R^3}{\underset{\displaystyle \underset{O}{\parallel}}{\square}}-\text{N}-R^2 \quad (I)$$

| Ex. | R¹ | R² | R³ | IR and ¹HNMR Data |
|---|---|---|---|---|
| 38 | PhCH₂ | [CH₂SO₂Ph / =C(CH₃)– / CH₂SO₂Ph with CO₂CH₂Ph] | benzothiazol-2-yl | IR (CHCl₃) 3380, 1777, 1717, 1670 cm⁻¹<br>NMR (CDCl₃, δ) 3.63 (bs, 2H),<br>4.11 (d, 1H, 15Hz), 4.55–5.14 (m, 5H),<br>5.32 (d, 1H, 5Hz), 5.38 (d, 1H, 14Hz),<br>6.57 (d, 1H, 8Hz), 7.10–8.00 (m, 24H) |
| 39 | PhCH₂ | [CH₂SCSOEt / =C(CH₃)– / CH₂SCSOEt with CO₂CH₂Ph] | benzothiazol-2-yl | IR (CHCl₃) 3380, 1778, 1714, 1669 cm⁻¹<br>NMR (CDCl₃, δ) 1.38 (t, 6H, 7Hz),<br>3.66 (bs, 2H),<br>4.44 and 4.48 (ABq, 2H, 13Hz),<br>4.50 (bs, 2H), 4.62 (q, 4H, 7Hz),<br>4.93 (dd, 1H, 5Hz, 8Hz),<br>4.74 and 5.08 (ABq, 2H, 12Hz),<br>5.45 (d, 1H, 5Hz), 6.59 (d, 1H, 8Hz),<br>7.15 (s, 5H), 7.30 (s, 5H),<br>7.10–7.90 (m, 4H) |
| 40 | PhCH₂ | [CH₂SBT / =C(CH₃)– / CH₂SBT with CO₂CH₂Ph] | benzothiazol-2-yl | IR (CHCl₃) 3390, 1778, 1712, 1670 cm⁻¹<br>NMR (CDCl₃, δ) 3.56 (bs, 2H),<br>4.63 and 4.83 (ABq, 2H, 13Hz),<br>4.68 and 4.86 (ABq, 2H, 14Hz),<br>4.90 and 5.08 (ABq, 2H, 12Hz),<br>4.98 (dd, 1H, 5Hz, 8Hz), 5.48 (d, 1H, 5Hz),<br>6.62 (d, 1H, 8Hz), 7.10 (s, 5H),<br>7.23 (s, 5H), 7.00–7.90 (m, 12H) |
| 41 | PhCH₂ | [CH₂S-(1-methyl-tetrazol-5-yl) / =C(CH₃)– / CH₂S-(1-methyl-tetrazol-5-yl) with CO₂CH₂Ph] | benzothiazol-2-yl | IR (CHCl₃) 3400, 1780, 1720, 1672 cm⁻¹<br>NMR (CDCl₃, δ) 3.73 (bs, 2H), 8.86 (s, 3H),<br>8.89 (s, 3H), 4.59 and 4.75 (ABq, 2H, 14Hz),<br>4.63 (bs, 2H), 4.92 (dd, 1H, 5Hz, 8Hz),<br>4.99 and 5.13 (ABq, 2H, 12Hz),<br>5.48 (d, 1H, 5Hz), 7.17 (s, 5H),<br>7.32 (s, 5H), 7.20–7.99 (m, 5H) |
| 42 | PhCH₂ | [CH₂S-(1,3,4-thiadiazol-2-yl) / =C(CH₃)– / CH₂S-(1,3,4-thiadiazol-2-yl) with CO₂CH₂Ph] | benzothiazol-2-yl | IR (CHCl₃) 3400, 1777, 1717, 1683 cm⁻¹<br>NMR (CDCl₃, δ) 2.70 (bs, 6H), 3.75 (bs, 2H),<br>4.50 and 4.73 (ABq, 2H, 13Hz),<br>4.50 and 4.87 (ABq, 2H, 14Hz),<br>4.98 and 5.13 (ABq, 2H, 12Hz),<br>5.40–5.60 (m, 2H), 7.10 (s, 5H),<br>7.10–7.90 (m, 10H) |
| 43 | PhCH₂ | [CH₂Cl / =C(CH₃)– / CH₂Cl with CO₂Me] | benzothiazol-2-yl | IR (CHCl₃) 3400, 1780, 1720, 1671 cm⁻¹<br>NMR (CDCl₃, δ) 3.57 (s, 3H), 3.72 (s, 2H),<br>4.62 and 4.78 (ABq, 2H, 10Hz), 4.70 (s, 2H),<br>4.97 (dd, 1H, 5Hz, 7Hz), 5.58 (d, 1H, 5Hz),<br>6.63 (d, 1H, 7Hz), 7.33 (s, 5H),<br>7.20–7.90 (m, 4H) |
| 44 | PhCH₂ | [CH(CH₃)(CO₂Me) / =C< / CH₂CH₂Cl] | pyridin-2-yl | IR (CHCl₃) 3350, 1775, 1721, 1670 cm⁻¹<br>NMR (CDCl₃, δ) 3.55 (s, 2H), 3.71 (s, 3H),<br>4.24 (bs, 2H), 5.18 (s, 1H),<br>5.20–5.50 (m, 3H), 5.48 (s, 1H),<br>7.00–7.70 (m, 8H), 8.40 (bd, 2H, 5.5Hz) |

TABLE 5-continued $$\text{(I)}$$

Structure (I): β-lactam with $R^1C(O)NH$- and $-S-S-R^3$ substituents on the azetidinone ring, N-substituted with $R^2$.

| Ex. | $R^1$ | $R^2$ | $R^3$ | IR and $^1$HNMR Data |
|---|---|---|---|---|
| 45 | PhCH$_2$ | –CH(CO$_2$Me)–C(=CH–CH$_2$Cl)– | Ph | IR (CHCl$_3$) 3380, 1770, 1730, 1680 cm$^{-1}$ NMR (CDCl$_3$, δ) 3.51 (s, 2H), 3.68 (s, 3H), 4.10 (bs, 2H), 4.94 (s, 1H), 5.11 (s, 1H), 5.20–5.50 (m, 3H), 6.12 (d, 1H, 8Hz), 7.10–7.60 (m, 10H) |
| 46 | PhCH$_2$ | –CH(CO$_2$Me)–C(=CH–CH$_2$Cl)– | 5-methyl-1,3,4-thiadiazol-2-yl | IR (CHCl$_3$) 3280, 1775, 1720, 1675 cm$^{-1}$ NMR (CDCl$_3$, δ) 2.70 (s, 3H), 3.66 (s, 2H), 3.79 (s, 3H), 4.26 (bs, 2H), 5.05–5.35 (m, 3H), 5.56 (s, 1H), 5.62 (d, 1H, 4.5Hz), 7.00 (d, 1H, 9Hz), 7.32 (s, 5H) |
| 47 | PhCH$_2$ | –CH(CO$_2$Me)–C(=CH–CH$_2$Cl)– | 1-phenyl-1H-tetrazol-5-yl | IR (CHCl$_3$) 3390, 1770, 1735, 1658 cm$^{-1}$ NMR (CDCl$_3$, δ) 3.62 (s, 2H), 3.74 (s, 3H), 4.23 (bs, 2H), 5.14 (dd, 1H, 5Hz, 8Hz), 5.25 (s, 1H), 5.34 (s, 1H), 5.50 (s, 1H), 5.61 (d, 1H, 5Hz), 6.90 (d, 1H, 8Hz), 7.23 (s, 5H), 7.55 (bs, 5H) |
| 48 | PhCH$_2$ | –CH(CO$_2$Me)–C(=CH–CH$_2$Cl)– | 1-methyl-1H-tetrazol-5-yl | IR (CHCl$_3$) 3390, 1780, 1725, 1660 cm$^{-1}$ NMR (CDCl$_3$, δ) 3.60 (s, 2H), 3.77 (s, 3H), 3.97 (s, 3H), 4.24 (bs, 2H), 5.10 (dd, 1H, 5Hz, 8Hz), 5.21 (s, 2H), 5.47 (s, 1H), 5.66 (d, 1H, 5Hz), 7.04 (d, 1H, 8Hz), 7.26 (s, 5H) |
| 49 | PhCH$_2$ | –CH(CO$_2$Me)–C(=CH–CH$_2$Cl)– | 4-NO$_2$–C$_6$H$_4$– | IR (CHCl$_3$) 3390, 1785, 1730, 1670 cm$^{-1}$ NMR (CDCl$_3$, δ) 3.70 (s, 2H), 3.80 (s, 3H), 4.27 (bs, 2H), 5.17 (s, 1H), 5.25–5.45 (m, 3H), 5.61 (s, 1H), 6.72 (bd, 1H, 8Hz), 7.37 (s, 5H), 7.51 (d, 2H, 9Hz), 8.12 (d, 2H, 9Hz) |
| 50 | PhCH$_2$ | –CH(CO$_2$Me)–C(=CH–CH$_2$Cl)– | benzothiazol-2-yl | IR (CHCl$_3$) 3280, 1775, 1740, 1665 cm$^{-1}$ NMR (CDCl$_3$, δ) 3.69 (s, 3H), 4.16 and 4.40 (ABq, 2H, 12Hz), 5.21 (dd, 1H, 5Hz, 8Hz), 5.30 (bs, 2H), 5.53 (d, 1H, 5Hz), 5.56 (s, 1H), 7.02 (d, 1H, 8Hz), 7.20–7.60 (m, 7H), 7.55–7.95 (m, 2H) |
| 51 | PhCH$_2$ | –CH(CO$_2$CH$_2$Ph)–C(=CH–CH$_2$Cl)– | 4-NO$_2$–C$_6$H$_4$– | IR (CHCl$_3$) 3380, 1780, 1735, 1680 cm$^{-1}$ NMR (CDCl$_3$, δ) 3.65 (s, 2H), 4.22 (bs, 2H), 5.20 (s, 2H), 5.05–5.40 (m, 4H), 5.53 (s, 1H), 6.81 (bd, 1H, 8Hz), 7.34 (s, 10H), 7.42 (d, 2H, 9Hz), 8.05 (d, 2H, 9Hz) |
| 52 | PhCH$_2$ | –CH(CO$_2$CH$_2$Ph)–C(=CH–CH$_2$Cl)– | 5-methyl-1,3,4-thiadiazol-2-yl | IR (neat) 3280, 1775, 1740, 1665 cm$^{-1}$ NMR (CDCl$_3$, δ) 2.62 (s, 3H), 3.60 (s, 2H), 4.21 (bs, 2H), 5.05–5.40 (m, 3H), 5.16 (s, 2H), 5.46 (s, 1H), 5.55 (d, 1H, 4.5Hz), 7.10–7.45 (m, 11H) |
| 53 | PhCH$_2$ | –CH(CO$_2$CH$_2$Ph)–C(=CH–CH$_2$Cl)– | 2,3,4,5-tetrachlorophenyl | IR (neat) 3260, 1770, 1735, 1655 cm$^{-1}$ NMR (CDCl$_3$, δ) 3.55 (s, 2H), 4.24 (bs, 2H), 4.96 (s, 1H), 5.05–5.40 (m, 3H), 5.27 (s, 2H), 5.68 (d, 1H, 5Hz), 6.16 (d, 1H, 8Hz), 7.15–7.45 (m, 10H) |
| 54 | PhOCH$_2$ | –CH(CO$_2$CH$_2$Ph)–C(=CH–CH$_2$Cl)– | 5-methyl-1,3,4-thiadiazol-2-yl | IR (neat) 3310, 1780, 1745, 1685 cm$^{-1}$ NMR (CDCl$_3$, δ) 2.63 (s, 3H), 4.27 (bs, 2H), 4.58 (s, 2H), 5.24 (s, 2H), 5.20–5.60 (m, 4H), 5.70 (d, 1H, 5Hz), 6.70–7.60 (m, 11H) |

TABLE 5-continued $$\text{R}^1\text{CNH} \begin{array}{c} \text{O} \\ \| \\ \end{array} \begin{array}{c} \text{S—S—R}^3 \\ \end{array} \begin{array}{c} \\ \text{N} \\ \text{R}^2 \end{array} \quad \text{(I)}$$

| Ex. | R¹ | R² | R³ | IR and ¹HNMR Data |
|---|---|---|---|---|
| 55 | PhOCH$_2$ | CH(CH$_3$)(CO$_2$CH$_2$Ph)–C(=CH$_2$)–CH$_2$Cl | 2,3,4,5-tetrachlorophenyl | IR (neat) 3300, 1775, 1740, 1680 cm$^{-1}$<br>NMR (CDCl$_3$, δ) 4.17 (bs, 2H), 4.38 (bs, 2H),<br>5.02 (s, 1H), 5.20 (s, 2H),<br>5.20–5.50 (m, 3H), 5.80 (d, 1H, 5Hz),<br>6.70–7.50 (m, 11H) |
| 56 | PhCH$_2$ | CH(CH$_3$)(CO$_2$CH$_2$Ph)–C(=CH$_2$)–CH$_2$Cl | benzimidazol-2-yl | IR (neat) 3160, 1770, 1735, 1650 cm$^{-1}$<br>NMR (CDCl$_3$, δ) 3.63 (s, 2H), 4.10 (s, 2H),<br>5.18 (s, 2H), 5.10–5.60 (m, 5H),<br>7.00–7.70 (m, 15H), 8.03 (bd, 1H, 6Hz) |
| 57 | PhCH$_2$ | CH(CH$_3$)(CO$_2$CH$_2$Ph)–C(=CH$_2$)–CH$_2$ONO$_2$ | benzothiazol-2-yl | IR (CHCl$_3$) 3280, 1780, 1740, 1670,<br>1640, 1270 cm$^{-1}$<br>NMR (CDCl$_3$, δ) 3.66 (s, 2H), 5.10 (s, 2H),<br>5.14 (s, 2H), 5.00–5.30 (m, 2H),<br>5.40 (s, 1H), 5.51 (d, 1H, 5Hz),<br>5.56 (s, 1H), 6.56 (d, 1H, 7.5Hz),<br>7.10–7.60 (m, 12H), 7.68–8.00 (m, 2H) |

EXAMPLE 58

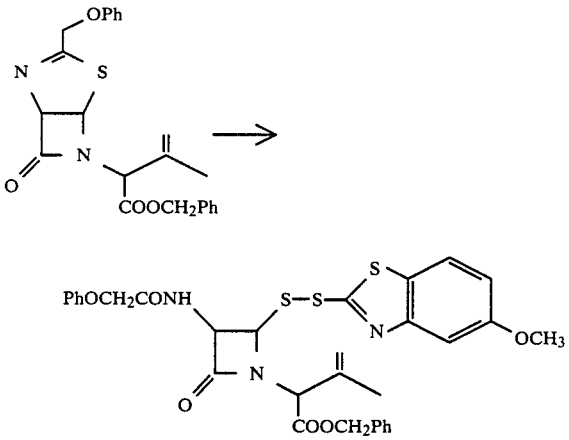

Dispersed in 3 ml of tetrahydrofuran were 60 mg of benzyl 2-(3-phenoxymethyl-7-oxo-4-thia-2,6-diazabicyclo[3,2,0]hepto-2-ene-6-yl)-3-methyl-3-butenate and 62 mg of 5,5'-dimethoxybenzothiazolyldisulfide. To the solution was added 0.75 ml of a 5% aqueous solution of hydrochloric acid and the mixture was stirred at room temperature for 40 minutes.

To the reaction mixture was added 10 ml of ethyl acetate and the insolubles were removed by a glass filter. The filtrate was washed with water and dried over anhydrous sodium sulfate. The solvent was distilled off.

The resulting residue was separated and purified by silica gel column chromatography, giving 78.5 mg of benzyl 2-(4-(5-methoxybenzothiazole-2-yl)dithio-3-phenylacetamide-2-oxo-azetidine-1-yl)-3-methyl-2-butenate in 87% yield.

NMR (CDCl$_3$): δ(ppm): 1.94 (s, 3H), 3.81 (s, 3H), 4.48 and 4.55 (ABq, 2H, J=1.25 Hz), 4.98 (s, 1H), 5.02 (s, 1H), 5.17 (s, 3H), 5.20–5.70 (m, 2H), 6.70–7.60 (m, 14H).

EXAMPLES 59 TO 74

The procedure of Example 58 was followed to give the compounds (I) as shown in Table 6 below, which also indicates the yields and ¹HNMR data of the compound (I) thus obtained.

TABLE 6

$$\text{R}^1\text{CONH} \quad \text{S—S—R}^3$$
(β-lactam structure with N-CH(COOR)-C(=CH₂)CH₃ substituent)

| Ex. | R¹ | R | R³ | NMR (CDCl₃, δ, J=Hz) | Yield |
|---|---|---|---|---|---|
| 59 | PhOCH₂ | —CH₂—C₆H₅ | 6-NO₂-benzothiazol-2-yl | 1.98 (s, 3H), 4.59 (s, 2H), 5.01 (s, 1H), 5.04 (s, 1H), 5.19 (s, 2H), 5.22 (s, 1H), 5.45 (dd, 1H, J=4.8 and 8.1Hz), 5.65 (d, 1H, J=4.8Hz), 6.80–7.50 (m, 11H), 7.85 (d, 1H, J=9.0Hz), 8.26 (dd, 1H, J=2.3 and 9.0Hz), 8.54 (d, 1H, J=2.3Hz) | 89% |
| 60 | PhOCH₂ | —CH₂—CO—C₆H₄—Br | 6-CH₃-benzothiazol-2-yl | 2.03 (s, 2H), 2.40 (s, 3H), 4.46 and 4.53 (ABq, 2H, J=12.5Hz), 5.18 (s, 1H), 5.15–5.70 (m, 6H), 6.75–7.85 (m, 13H) | 89% |
| 61 | PhOCH₂ | —CH₂—(2,5-Cl₂-3,4,6-(OMe)₃-C₆) | 4-CH₃-benzothiazol-2-yl | 1.95 (s, 3H), 2.67 (s, 3H), 2.87 (s, 6H), 3.94 (s, 2H), 4.46 and 4.53 (ABq, 2H, J=12Hz), 4.95 (s, 1H), 5.10 (s, 1H), 5.15 (s, 1H), 5.30–5.70 (m, 4H), 6.70–7.60 (m, 9H) | 88% |
| 62 | PhOCH₂ | —CH₂—(3,4,5-(OMe)₃-C₆H₂) | benzothiazol-2-yl | 1.94 (s, 3H), 3.82 (s, 9H), 4.51 (bs, 2H), 4.44 (s, 1H), 5.01 (s, 1H), 5.06 (s, 2H), 5.14 (s, 1H), 5.30–5.65 (m, 2H), 6.50 (s, 2H), 6.75–7.85 (m, 10H) | 82% |
| 63 | PhOCH₂ | —CH₂—C₆H₄—OMe | benzothiazol-2-yl | 1.93 (s, 3H), 3.75 (s, 3H), 4.50 (bs, 2H), 4.93 (s, 1H), 4.96 (s, 1H), 5.08 (s, 2H), 5.13 (bs, 1H), 5.42 (dd, 1H, J=4.0 and 6.5Hz), 5.56 (d, 1H, J=4Hz), 6.65–7.90 (m, 14H) | 91% |
| 64 | PhOCH₂ | 9-fluorenyl | benzothiazol-2-yl | 1.96 (s, 3H), 4.58 and 4.52 (ABq, 2H, J=12.5Hz), 5.04 (s, 1H), 5.20 (bs, 2H), 5.52 (dd, 1H, J=4.8 and 8.3Hz), 5.63 (d, 1H, J=4.8Hz), 6.79 (s, 1H), 6.80–7.90 (m, 18H) | 83% |
| 65 | PhOCH₂ | —CH₂OCH₃ | benzothiazol-2-yl | 1.97 (s, 3H), 3.94 (s, 3H), 4.49–4.54 (ABq, 2H, J=12Hz), 4.75–5.25 (m, 5H), 5.45 (dd, 1H, J=4.0 and 6.5Hz), 5.58 (d, 1H, J=4.0Hz), 6.75–7.90 (m, 10H) | 45% |
| 66 | PhOCH₂ | —CHOCH₂CH₂ (OCH₃) | benzothiazol-2-yl | 1.97 (s, 3H), 3.85 (s, 3H), 2.35–3.60 (m, 2H), 3.60–3.85 (m, 2H), 4.54 (s, 2H), 4.75–5.75 (m, 7H), 6.75–7.90 (m, 10H) | 53% |
| 67 | PhCH₂ | —CH₂—C₆H₄—OMe | benzothiazol-2-yl | 1.89 (s, 3H), 3.67 (s, 2H), 3.74 (s, 3H), 4.87 (s, 1H), 4.94 (s, 1H), 5.05 (s, 2H), 5.09 (bs, 1H), 5.25 (dd, 1H, J=4.0 and 7.0Hz), 5.45 (d, 1H, J=4.0Hz), 6.45 (d, 1H, J=7.0Hz), 6.55–7.90 (m, 13H) | 88% |

TABLE 6-continued

| Ex. | R¹ | R | R³ | NMR (CDCl₃, δ, J=Hz) | Yield |
|---|---|---|---|---|---|
| 68 | PhCH₂ | 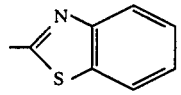 | 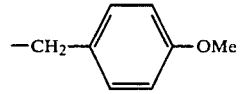 | 1.92 (s, 3H), 3.67 (s, 2H), 4.98 (s, 1H), 5.16 (bs, 2H), 5.35 (dd, 1H, J=4.7 and 8.1Hz), 5.52 (d, 1H, J=4.7Hz), 6.31 (d, 1H, J=8.1Hz), 6.75 (s, 1H), 7.1-7.9 (m, 18H) | 82% |
| 69 | PhCH₂ | —CH₂—⟨C₆H₄⟩—OMe | 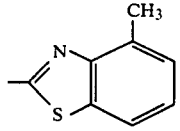 | 1.91 (s, 3H), 2.65 (s, 2H), 3.66 (s, 2H), 3.75 (s, 3H), 4.90 (s, 1H), 4.96 (s, 1H), 5.07 (s, 2H), 5.13 (bs, 1H), 5.28 (dd, 1H, J=4.8 and 3.1Hz), 5.52 (d, 1H, J=4.8Hz), 6.10 (d, 1H, J=8.1Hz), 6.80 (d, 2H, J=8.8Hz), 7.00-7.70 (m, 10H) | 90% |
| 70 | PhCH₂ | —CH₂—⟨C₆H₄⟩—NO₂ | 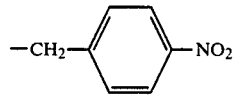 | 1.91 (s, 3H), 3.66 (s, 2H), 4.90 (s, 1H), 4.96 (s, 1H), 5.16 (s, 2H), 5.26 (dd, 1H, J=4.0 and 9.0Hz), 5.39 (d, 1H, J=4.0Hz), 6.18 (d, 1H, J=9.0Hz), 7.20-7.90 (m, 11H), 8.10 (d, 2H, J=9.0Hz) | 89% |
| 71 | PhCH₂ | —CH₂—⟨C₆H₄⟩(o-NO₂) | 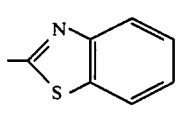 | 1.95 (s, 2H), 3.69 (s, 2H), 4.94 (s, 1H), 5.02 (s, 1H), 5.15 (s, 1H), 5.20-5.60 (m, 4H), 6.31 (d, 1H, J=9.0Hz), 7.30-8.10 (m, 13H) | 88% |
| 72 | PhOCH₂ | —CH(COCH₃)(COOCH₃) | 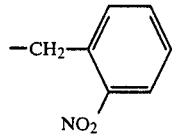 | 2.00 (s, 3H), 2.32 (s, 3H), 3.28 (bs, 2H), 4.53 (bs, 2H), 5.09 (bs, 1H), 5.24 (bs, 2H), 5.40-5.60 (m, 2H), 6.75-8.00 (m, 10H) | 79% |
| 73 | PhOCH₂ | PhCH₂ | 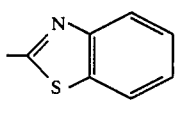 | 1.96 (s, 3H), 4.56 (s, 2H), 4.95 (s, 1H), 4.98 (s, 1H), 5.16 (s, 2H), 5.42 (dd, 1H, J=4.0 and 7.0Hz), 5.59 (d, 1H, J=4.0Hz), 6.65-7.35 (m, 11H), 7.49 (d, 1H, J=8.0Hz), 7.71 (d, 1H, J=8.0Hz), 8.05 (s, 1H) | 85% |
| 74 | PhOCH₂ | PhCH₂ | 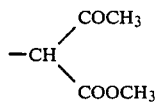 | 1.94 (s, 3H), 2.63 (s, 3H), 4.46 and 4.53 (ABq, 2H, J=13Hz), 4.93 (s, 1H), 4.96 (s, 1H), 5.19 (s, 3H), 5.43 (dd, 1H, J=4.0 and 8.0Hz), 5.57 (d, 1H, J=4.0Hz), 6.75-7.50 (m, 14H) | 86% |

REFERENCE EXAMPLE

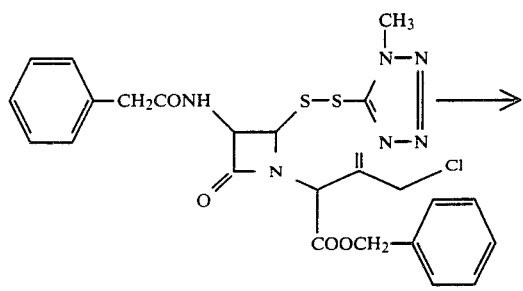

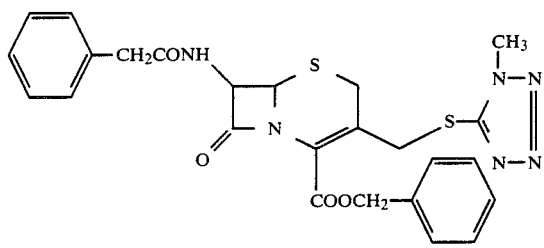

Dimethylformamide (0.5 ml) was added to 30 mg of benzyl 2-(3-phenylacetamide-4-((1-methyltetrazole-5-yl)thio)-2-azetidinone-1-yl)-3-chloromethyl-3-butenate to obtain a uniform solution. The solution was cooled to $-25°$ C. Thereto was added 40 ml of a about 2M solution of ammonia gas dissolved in dimethylformamide and the mixture was stirred for 1 hour. Four drops of 5% aqueous solution of hydrochloric acid were added and the mixture was vigorously agitated to warm to room temperature. The resulting mixture was diluted with 5 ml of ethyl acetate. The dilute was washed with a saturated aqueous solution of sodium chloride, dried over $Na_2SO_4$ and concentrated. The residue thus obtained was subjected to silica gel column chromatography using a 15:1 benzeneethyl acetate mixture, giving 20.8 mg of benzyl 7-phenylacetamide-3-((1-methyltetrazole-5-yl)thiomethyl)-3-cephem-4-carboxylate.

The compound thus prepared was chemically analyzed with the following result.

IR (nujol): 3265, 1780, 1710, 1655 cm$^{-1}$.

NMR (CDCl$_3$): δ(ppm) 3.63 (s, 2H), 3.70 (s, 2H), 3.90 (s, 3H), 4.24 and 4.53 (ABq, 2H, 14 Hz), 4.95 (d, 1H, 5 Hz), 5.31 (s, 2H), 5.85 (dd, 1H, 5 Hz, 9 Hz), 6.21 (d, 1H, 9 Hz), 7.32 (s, 5H), 7.40 (s, 5H).

We claim:

1. A process for preparing an azetidinone compound represented by the formula

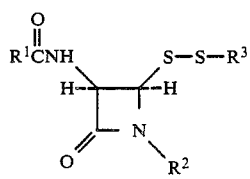

(I)

wherein R$^1$ represents a straight-chain or branched-chain lower alkyl group, phenyl, p-nitrophenyl, p-chlorophenyl, benzyl, p-nitrophenylmethyl, p-chlorophenylmethyl, p-methoxyphenylmethyl, diphenylmethyl, phenoxymethyl, p-nitrophenoxymethyl or p-chlorophenoxymethyl, R$^2$ represents hydrogen, acetyl, propionyl, butyryl, trimethylsilyl, dimethylbutylsilyl, methanesulfonyl, ethanesulfonyl, phenylsulfonyl, p-toluenesulfonyl, diphenylphosphonyl, dibenzylphosphonyl, diethylphosphonyl, or a group represented by the formula

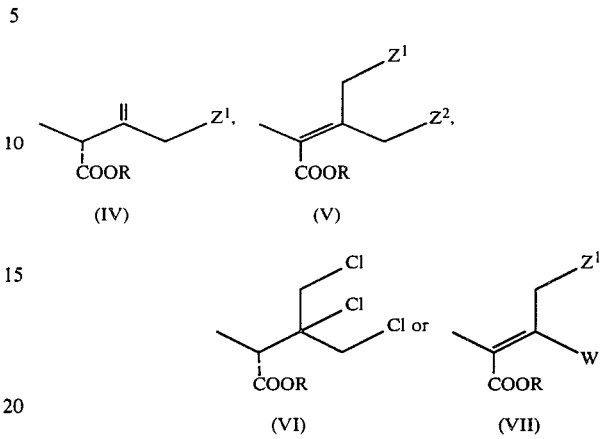

wherein R is hydrogen or a carboxyl-protecting group, Z$^1$ and Z$^2$ are the same or different and are each hydrogen, a halogen, methylthio, ethylthio, phenylthio, p-nitrophenylthio, pentachlorophenylthio, 2-pyridylthio, 2-benzothiadiazolylthio, 1,3,4-thiadiazole-5-ylthio, 2-substituted-1,3,4-thiadiazole-5 -ylthio, 1,2,3,4-tetrazole-5-ylthio, 1-substituted-1,2,3,4-tetrazole-5-ylthio, ethoxythiocarbonylthio, N,N-diethyldithiocarbamate, N,N-dimethyldithiocarbamate, phenylsulfonyl, p-methylphenylsulfonyl, hydroxy, methoxy, ethoxy, acetoxy, benzoyloxy, nitrosoxy, nitryloxy, dimethylamino or piperidine-1-yl, and W is a protected hydroxyl group, and R$^3$ represents phenyl, p-nitrophenyl, pentachlorophenyl or a group formed by eliminating one hydrogen atom from an aromatic heterocyclic compound containing a single heterocyclic ring (optionally fused to a benzene ring) of 5–6 members with no more than 4 heteroatoms selected from the group consisting of nitrogen and sulfur, said aromatic heterocyclic compound optionally having methyl, nitro, methoxy, —CF$_3$ or phenyl as a substituent, said process comprising reacting a thiazolinoazetidinone compound represented by the formula

(II)

wherein R$^1$ and R$^2$ are as defined above with a sulphur-containing compound represented by the formula

R$^3$—S—Y        (III)

wherein R$^3$ is as defined above and Y represents —SR$^3$ (in which R$^3$ is as defined above), diethylamino, diisopropylamino, cyclohexylamino, morpholino, piperidino, pyrrolidino, phthalimido or succinimido in the presence of an acid in a hydrous organic solvent.

2. A process as defined in claim 1 in which the compound (III) is used in an amount of about 1 to about 10 moles per mole of the compound of the formula (II).

3. A process as defined in claim 1 or 2 in which the acid is a mineral acid, sulfonic acid, α-halocarboxylic acid or polycarboxylic acid.

4. A process as defined in claim 1 or 2 in which the acid is a member selected from the class consisting of perchloric acid, trifluoroacetic acid, trichloroacetic acid, dichloroacetic acid, trifluoromethanesulfonic acid, trichloromethanesulfonic acid, hydrochloric acid, hydrobromic acid, sulphuric acid, hydrofluoric acid, nitric acid, phosphoric acid, benzenesulfonic acid and toluenesulfonic acid.

5. A process as defined in any one of claims 1 or 2 in which the compound of the formual (II) is one wherein $R^1$ is benzyl, phenoxymethyl, p-chlorophenoxymethyl or phenyl.

6. A process as defined in any one of claims 1 to 5 in which the compound of formula (II) is one wherein $R^2$ is hydrogen,

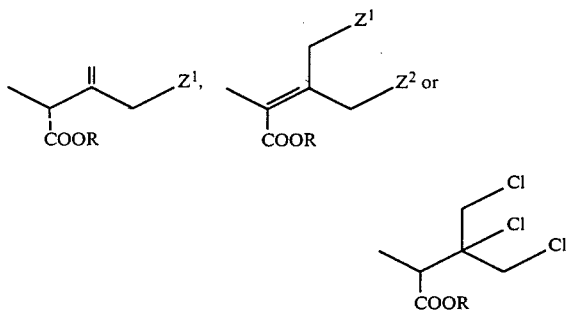

(in which R is hydrogen or a carboxyl-protecting group, and $Z^1$ and $Z^2$ are the same or different and are each hydrogen, halogen, methylthio, ethylthio, phenylthio, p-nitrophenylthio, pentachlorophenylthio, 2-pyridylthio, 2-benzothiadiazolylthio, 1,3,4-thiadiazole-5-ylthio, 2-methyl-1,3,4-thiadiazole-6-ylthio, 1,2,3,4-tetrazole-5-ylthio, 1-phenyl-1,2,3,4-tetrazole-5-ylthio, 1-methyl-1,2,3,4-tetrazole-5-ylthio, ethoxythiocarbonylthio, N,N-diethyldithiocarbamate, N,N-dimethyldithiocarbamate, phenylsulfonyl, p-methylphenylsulfonyl, hydroxy, methoxy, ethoxy, acetoxy, benzoyloxy, nitrosoxy, nitryloxy, dimethylamino or piperidine-1-yl).

7. A process as defined in claim 1 in which the compound of formula (III) is one wherein Y is $-SR^3$ (in which $R^3$ is benzothiazolyl-1-yl, 5-methyl-1,3,4-thiazolyl-2-yl, 5-phenyl-1,3,4-thiazolyl-2-yl or benzoimidazolyl-2-yl).

8. A process as defined in claim 1 wherein $R^3$ is phenyl, p-nitrophenyl, pentachlorophenyl, or a group formed by eliminating one hydrogen atom from an aromatic heterocyclic compound selected from the group consisting of pyridine, benzimidazole, benzothiazole, tetrazole and thiadiazole, said aromatic heterocyclic compound being optionally substituted with methyl, methoxy, nitro, phenyl or trifluoromethyl.

9. A process as defined in claim 1 wherein $R^3$ is phenyl, p-nitrophenyl, pentachlorophenyl, 2-benzothiazolyl, 5-methoxybenzothiazole-2-yl, 5-nitro-benzothioazole-2-yl, 5-methylbenzothiazole-2-yl, 5-trifluoromethyl-benzothiazole-2-yl, 7-methyl-benzothiazole-2-yl, 2-benzoimidazolyl, 2-pyridyl, 1,2,3,4-tetrazole-5-yl, 1-phenyl-1,2,3,4-tetrazole-5-yl, 1-methyl-1,2,3,4-tetrazole-5-yl, 2-methyl-1,3,4-thiadiazole-5-yl or 2-phenyl-1,3,4-thiadiazole-5-yl.

* * * * *